United States Patent [19]

Okumoto

[11] 4,292,522

[45] Sep. 29, 1981

[54] MATERIAL DENSITY RADIOLOGICAL MEASUREMENT SYSTEM WITH SUBSTANTIALLY LINEAR OUTPUT

[75] Inventor: Yutaka Okumoto, Tokyo, Japan

[73] Assignee: The Japan Tobacco & Salt Public Corporation, Tokyo, Japan

[21] Appl. No.: 103,860

[22] Filed: Dec. 14, 1979

[30] Foreign Application Priority Data

Dec. 20, 1978 [JP] Japan .................................. 53-156353

[51] Int. Cl.³ ........................ G01N 23/00; A24C 5/32
[52] U.S. Cl. ............................... 250/358 R; 250/308; 250/359
[58] Field of Search .............. 250/358 R, 359, 308, 250/360; 364/573; 328/144, 159; 131/21 B, 22 R

[56] References Cited

U.S. PATENT DOCUMENTS

| | | | |
|---|---|---|---|
| 3,529,162 | 9/1970 | Troutman | 250/358 R |
| 3,779,378 | 12/1973 | Scherf | 250/358 R |
| 3,864,573 | 2/1975 | Hoffman et al. | 250/358 R |
| 4,064,396 | 12/1977 | Panarello | 250/252 |

*Primary Examiner*—Alfred E. Smith
*Assistant Examiner*—Carolyn E. Fields
*Attorney, Agent, or Firm*—Lackenbach, Lilling & Siegel

[57] ABSTRACT

A material density radiological measurement system is provided. The system comprises a material density radiological detector, a squaring circuit connected to the output terminal of the detector, a constant multiplying circuit connected to the output terminal of the squaring circuit, and a subtracting circuit connected to the material density radiological detector and the constant multiplying circuit. The system eliminates the nonlinearity of the relationship between the ionization current and the density of tobacco during a measuring operation of tobacco density of a cigarette.

3 Claims, 5 Drawing Figures

MATERIAL DENSITY RADIOLOGICAL MEASUREMENT SYSTEM WITH SUBSTANTIALLY LINEAR OUTPUT

BACKGROUND OF THE INVENTION

The present invention relates to a material density measurement system using radioactive rays, particularly for providing a substantially linear output signal.

The relationship between the ionization current y and the density x of a material interrupting the radioactive rays is nonlinear and expressed in the following equation:

$$y = ke^{-\mu x}$$

where k and $\mu$ are constants.

In order to avoid the dificculty in handling the nonlinearity, there have been proposed various devices for converting an ionization current signal into a linear signal.

For instance, U.S. Pat. No. 3,529,162 discloses a device which approximates, making use of diode characteristics, the input/output characteristics with a plurality of polygonal lines. Also, the magazine TOBACCO INTERNATIONAL (Apr. 30, 1976) discloses a system which converts a nonlinear output signal into digital signals for processing. Further, a device referred to as a "log amplifier" is adapted to produce an output signal proportional to the logarithm of input voltage using analog elements.

The device making use of diode characteristics for approximating the output with a plurality of polygonal lines, however, has a drawback in that it is difficult to obtain an accurate approximation. The system incorporating a computer for processing digital signals requires a complicated circuit which considerably increases the system cost. Further, the device incorporating the log amplifier inconveniently exhibits a large fluctuation in output caused by temperature drift. The influence of the temperature drift is serious particularly when the changes in the input and output signals are small.

SUMMARY OF THE INVENTION

It is, therefore, an object of the present invention to provide a system for measuring the density of a material using radioactive rays, capable of converting the output of the radiation type density detector into an accurate linear signal, thereby to overcome the above-described problem of the prior art.

This object is accomplished by a material density radiorogical measurement system comprising a material density radiological detector having a radiation source for density measurement, an ionization chamber for density measurement, and a means for generating a reference density signal, said detector producing an output signal from a difference of an output signal of said ionization chamber for density measurement and said reference density signal; a squaring circuit connected to the output terminal of said detector; a constant multiplying circuit connected to the output terminal of said squaring circuit, said constant being predetermined to have a value which is smaller than the reciprocal of an ionization current obtained when the density of a material to be measured is equal to the reference density; and a subtracting circuit, which input terminals being connected to the output terminals of said detector and said constant multiplying circuit, respectively.

BRIEF DESCRIPTION OF THE DRAWINGS

Hereinafter, the invention will be described by way of example in more detail through an embodiment in which the invention is applied to a cigarette making machine, with reference to the accompanying drawings.

DETAILED DESCRIPTION OF THE PREFERRED EMBODIMENTS

Figure 1:
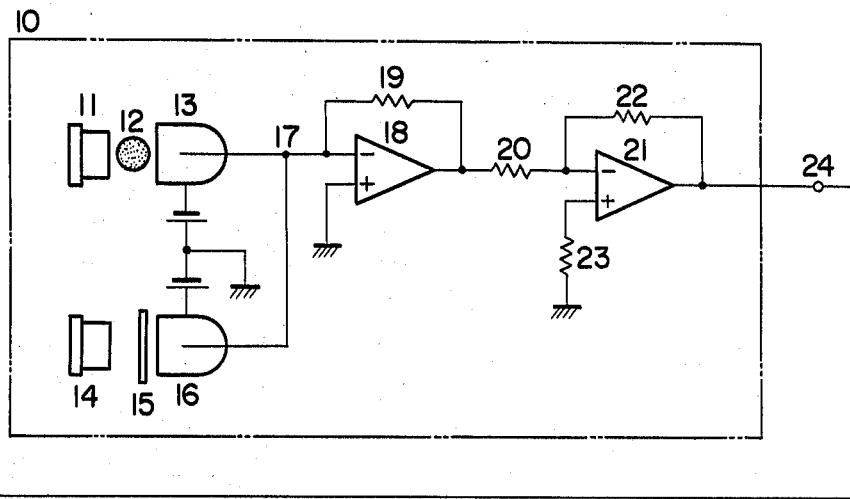
FIGS. 1 and 2 are the former and latter halves of a circuit diagram of the system according to this invention.
Figure 1:
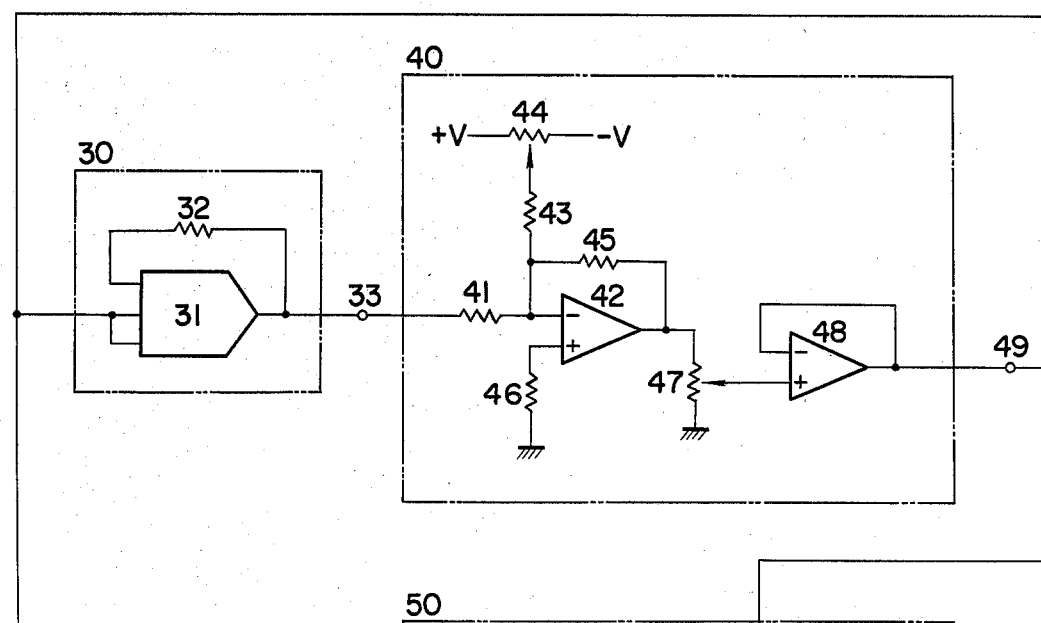
Figure 1:
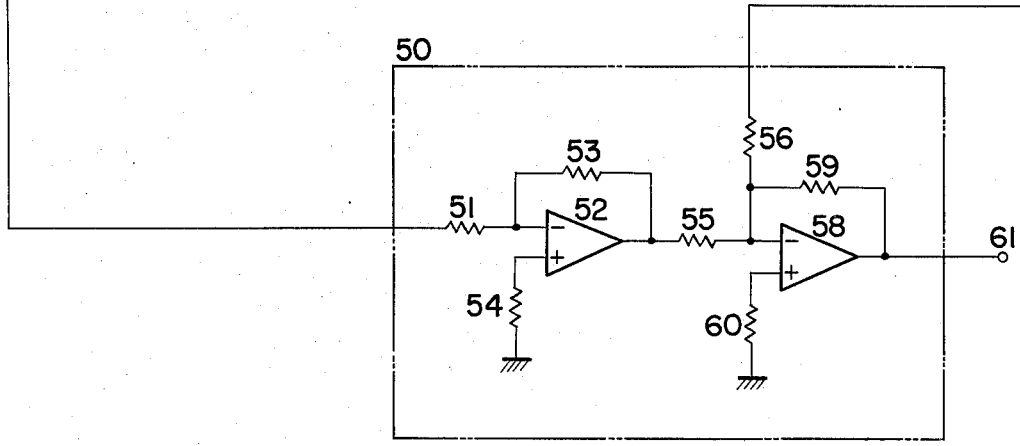
Figure 2:
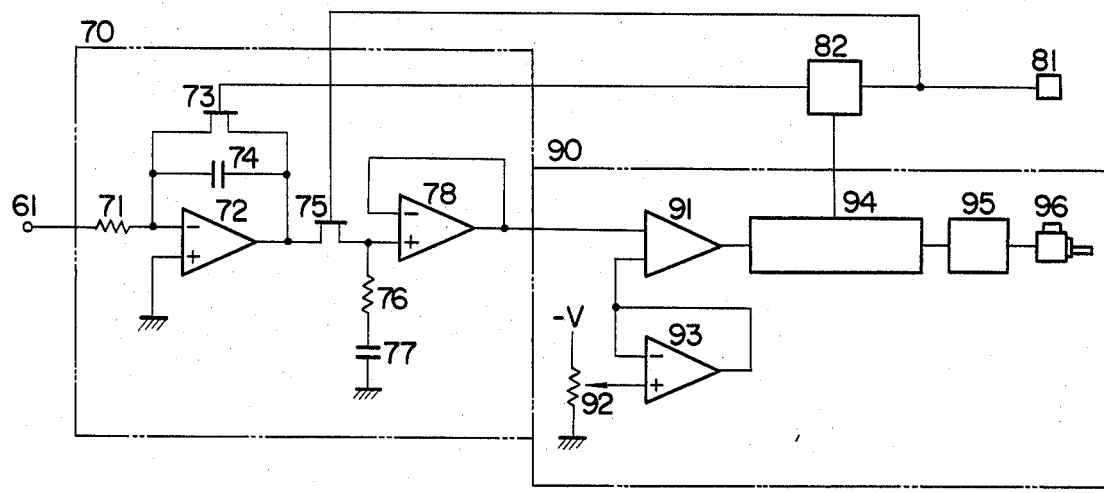

Referring to FIG. 1, reference numeral 10 generally designates a material density radiological detector when includes a radiation source 11 for density measurement, an ionization chamber 13 for the density measurement, the radiation source and ionization chamber being disposed on both sides of a specimen 12 which is in this case a continuous cigarette, and reference density signal generating device comprising a reference radiation source 14 and a reference ionization chamber 16 applied with a voltage of a polarity opposite to that of the ionization chamber 13, the reference radiation source 14 and reference ionization chamber 16 being disposed on both sides of a reference density material 15. The outputs from respective ionization chambers are delivered to a terminal 17 to which the inverted input terminal of operational amplifier 18 is connected. The inverted input terminal of an operational amplifier 21 is connected through a resistor 20 to the output terminal of the amplifier 18. Reference numeral 19, 22 and 23 denote resistors. The reference density material 15 is selected so that the voltage at the output 24 of the density detector 10 is 0 V when the density of the specimen equals the reference density.

A squaring circuit 30 connected to the output terminal of the density detector 10 comprising function generator 31 and resistor 32 produces an output proportional to the square of the input signal. This circuit is a conventional type such as Analog Multiplier 8013 produced by the Intersil Company Ltd.

A constant multiplying circuit generally designated at reference numeral 40 is connected to the output terminal 33 of the squaring circuit 30. The constant multiplying circuit 40 includes an operational amplifier 42 connected to the output terminal 33 through an input resistor 41 and an operation amplifier 48 connected to the output terminal of the operation amplifier 42 through a variable resistor 47. The variable resistor 47 is so adjusted that the input signal of the constant multiplying circuit 40 is multiplied by a constant which is not greater than the reciprocal of the ionization current obtained from the ionization chamber 13 when the density of a specimen equals the reference density, preferably a constant which equals the reciprocal of a value which is twice the ionization current value when the density of a specimen equals the reference density. Reference numeral 44 denotes a variable resistor, while reference numerals 43, 45 and 46 denote resistors.

A subtracting circuit generally designated at numeral 50 is connected to the output terminal 49 of the constant multiplying circuit 40 and to the output terminal 24 of the density detector 10 as shown in FIG. 1. The subtracting circuit 50 includes an operational amplifier 52 connected at its inverted input terminal to the output terminal 24 of the density detector through a resistor 51, an operational amplifier 58 connected at its inverted input terminal to the output terminal of the operational amplifier 52 through a resistor 55, and a resistor 56 which connects the inverted input terminal of the operational amplifier 58 to the output terminal 49 of the constant multiplying circuit 40. Resistors 53, 54 and resistors 59, 60 are connected, respectively, to the operational amplifiers 52 and 58.

The input of an integral holding circuit 70 is connected to the output terminal 61 of the subtracting circuit 50. The integral holding circuit 70 includes an operational amplifier 72 connected at its inverted input to the output terminal 61 of the subtracting circuit 50 through a resistor 71, a capacitor 74 and a switching element 73 which are connected between the inverted input and output terminals of the operational amplifier 72 and in parallel with each other, a switching element 75 connected at its switching terminals to the output terminal of the operational amplifier 72 and the non-inverted terminal of an operational amplifier 78, which terminal being connected to the ground through a resistor 76 and capacitor 77 which are connected in series. The output of the operational amplifier 78 is directly conncted to its inverted input.

A proximity switch 81 is adapted to produce, in synchronization with the operation of a cutting knife of a cigarette making machine, a single pulse for each rotation of a cutting knife. This pulse signal is delivered to the control input of the switching element 73 through a delay circuit 82. The output pulse signal is also delivered directly to the control input of the switching element 75. The time constant of the integral holding circuit 70 which is determined by the resistance 71 and the capacitor 74 is selected in accordance with the time required for one rotation of the cutting knife, i.e. the length of time required for the radioactive ray to scan the full length of one cigarette.

A circuit 90 for rejecting unsatisfactory cigarettes is at its input connected to the output of the integral holding circuit 70. The rejecting circuit 90 includes a reference voltage generating circuit comprising a variable resistor 92 and an operational amplifier 93, a comparator 91 having two input terminals to which the outputs of the reference voltage generating circuit and the integral holding circuit 70 are connected, a shift register 94 connected at its input to the output of the comparator 91 and adapted to receive a shift signal delivered by the delay circuit 82, a switching circuit 95 connected to the output of the shift register 94, and a rejecting valve 96 adapted to be activated by the switching circuit 95.

Figure 3:
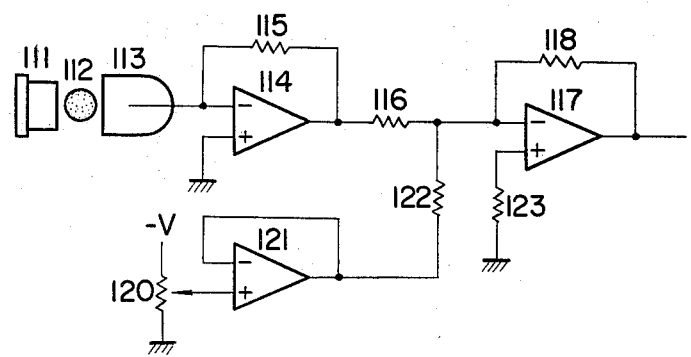
FIG. 3 is a circuit diagram of the second embodiment in regard to section 10 in FIG. 1.

As shown in FIG. 3, a density detector may be constituted with a radiation source 111 for the density measurement and, an ionization chamber 113 for the density measurement, the radiation source and ionizatin chamber being disposed on both sides of a specimen 112, an operational amplifier 114 connected at its inverted input to the output of the ionization chamber 113, an operational amplifier 117 connected at its inverted input to the output of the operational amplifier 114 through a resistor 116, resistors 115 and 118 which are connected between the inverted input and output terminals of the operational amplifiers 114 and 117, respectively, and a reference density signal generating device which consists of a variable resistor 120 with its movable point connected to the non-inverted input of an operational amplifier 121 whose output is directly connected to its invented input, its output being connected to the inverted input of the operational amplifier 117 through a resistor 122. The reference density signal generting device is adapted for generating an output voltage signal of a polarity opposite to that of the output voltage signal from the operational amplifier 114.

Figure 4:
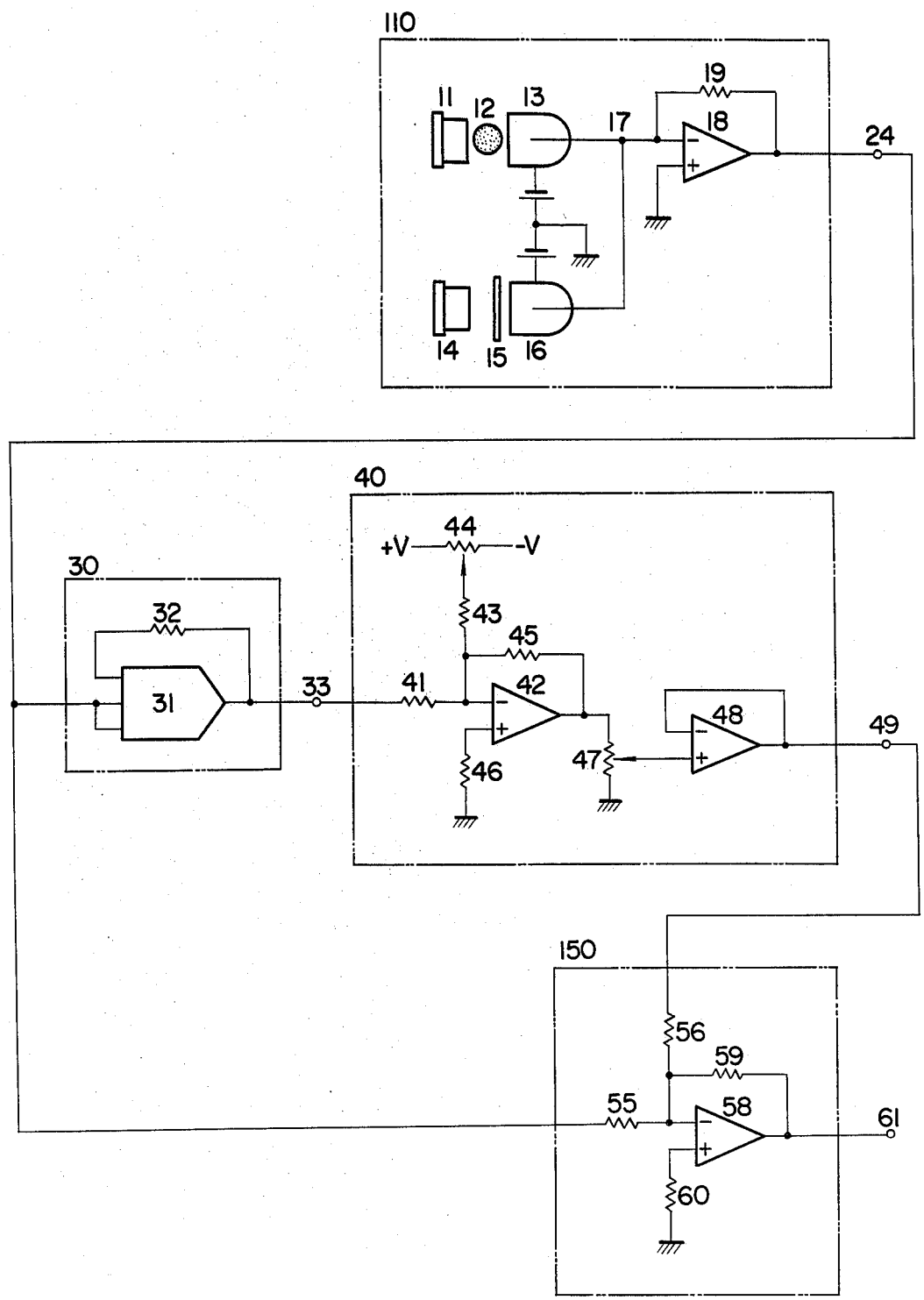
FIG. 4 is a circuit diagram of another embodiment in regard to FIG. 1.
Figure 5:
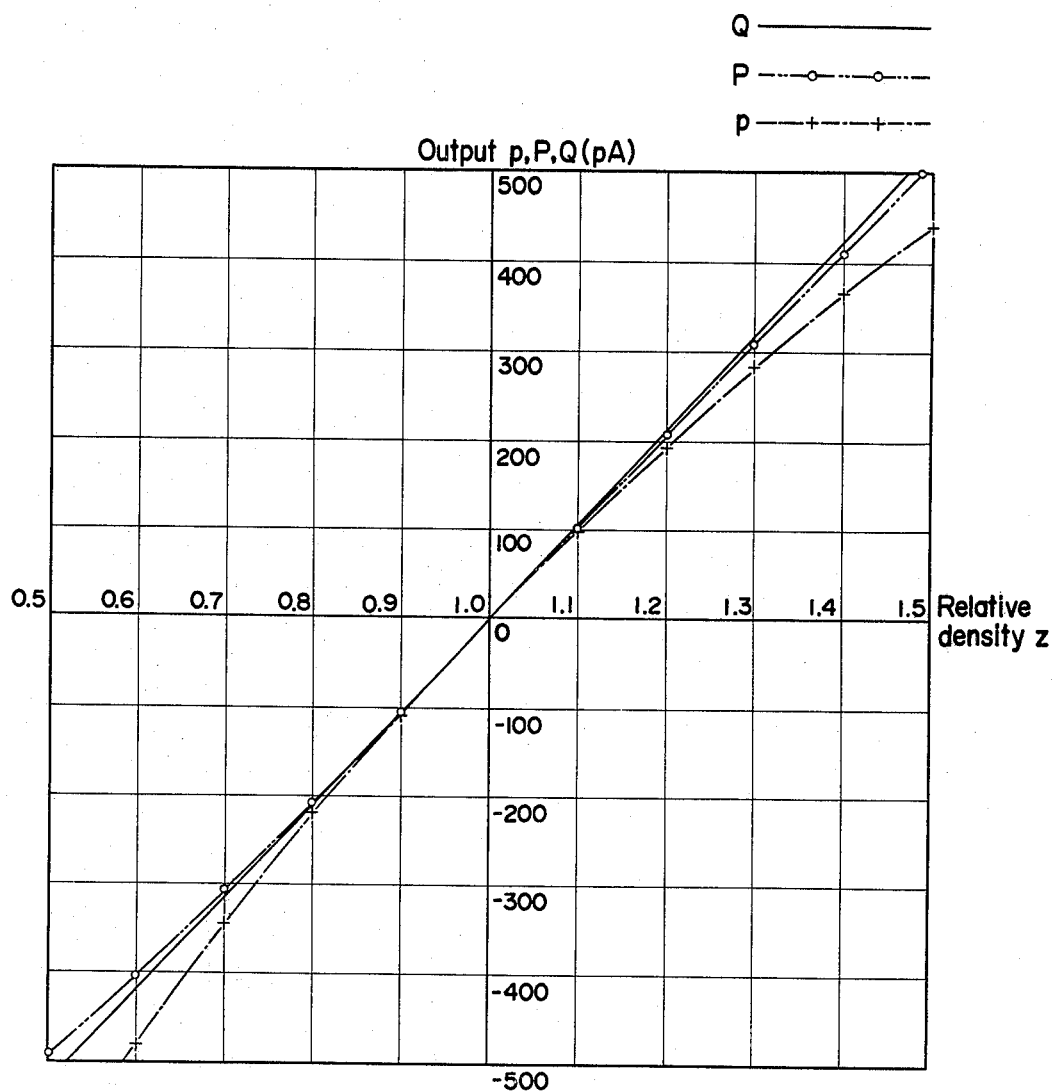
FIG. 5 shows the input/output characteristics of a system according to this invention.

It should be noted that the same operational result as obtained by the circuit shown in FIG. 1 can be obtained by a modified circuit shown in FIG. 4, where circuit blocks 110 and 150 take the place of circuit blocks 10 and 50 in FIG. 1, respectively. In FIG. 4, circuit components which function identically with those in FIG. 1 have the same reference numbers. As can be seen in FIG. 4, the output of the operational amplifier 18 in the block 110 is directly connected to the input resistance 55 of the operatinal amplifier 58 in the block 150, thus eliminating the operational amplifier 21, resistors 20, 22 and 23 in the block 10, and operational amplifier 52, resistors 51, 53 and 54 in the block 50 in FIG. 1. The circuit block 150, thus, functions as an adding circuit.

The embodiment of the invention having the described construction operates in the following manner. First, we define a word "relative density (z)" as the ratio of the densities of a specimen (x) and the reference material $(x_T)$; $z = x/x_T$.

Now, Io represents the ionization current in the absence of specimen and $I_T$ the current in the presence of the reference density material, then the relation between the ionization current I of the ionization chamber 13 for density measurement and the relative density z of a specimen will be given by the following equation (1).

$$I = f(z) = \text{Io} \exp\{\ln(I_T/\text{Io})z\} \quad (1)$$

An ionization current at point 17 is converted into a voltage by the operational amplifier 18, so that the value of a current is, from here, processed in the form of a voltage signal.

In the described embodiment, the relation between the output voltage p at the output terminal 24 representing the ionization current at point 17 and the relative density z of the specimen is given by the following equation (2), $$p = -3000 \exp\{\ln(-1500/-3000)z\} + 1500 \quad (2)$$

assuming that Io, $I_T$ and the ionization current of the reference ionization chamber are $-3000$ pA, $-1500$ pA and $1500$ pA, respectively.

According to the circuit of FIG. 1, if a constant to be multiplied by the multiplying circuit 40 is $\frac{1}{2}I_T$, the relation between the signal p and the output signal P obtained at the output terminal 61 is expressed by the following equation (3).

$$P = p - 1/2I_T p^2 \quad (3)$$

The linear output Q representing the density of a specimen is expressed by the line tangential to the equation (1) at the point $z = 1$ (reference density), i.e. by the following equation (4).

$$Q = \frac{d}{dz} f(z) = I_T \ln \frac{I_T}{I_0} \quad (4)$$
$$(z = 1)$$

Table 1 shows the output p, output P, the linear output Q and P/Q, with the relative density z being the variable.

TABLE 1

| z | p | P | Q | P/Q |
|---|---|---|---|---|
| 0.50 | −621.32 | −492.6 | −519.9 | 0.948 |
| 0.52 | −592.12 | −475.2 | −499.1 | 0.952 |
| 0.54 | −563.31 | −457.5 | −478.3 | 0.957 |
| 0.56 | −534.91 | −439.5 | −457.5 | 0.961 |
| 0.58 | −506.89 | −421.2 | −436.7 | 0.965 |
| 0.60 | −479.26 | −402.7 | −415.9 | 0.968 |
| 0.62 | −452.01 | −383.9 | −395.1 | 0.972 |
| 0.64 | −425.14 | −364.9 | −374.3 | 0.975 |
| 0.66 | −398.64 | −345.7 | −353.5 | 0.978 |
| 0.68 | −372.50 | −326.2 | −332.7 | 0.981 |
| 0.70 | −346.72 | −306.6 | −311.9 | 0.983 |
| 0.72 | −321.29 | −286.9 | −299.1 | 0.985 |
| 0.74 | −296.22 | −267.0 | −270.3 | 0.988 |
| 0.76 | −271.49 | −246.9 | −249.5 | 0.990 |
| 0.78 | −247.10 | −226.7 | −228.7 | 0.991 |
| 0.80 | −223.05 | −206.5 | −207.9 | 0.993 |
| 0.82 | −199.33 | −186.1 | −187.1 | 0.994 |
| 0.84 | −175.93 | −165.6 | −166.4 | 0.996 |
| 0.86 | −152.86 | −145.1 | −145.6 | 0.997 |
| 0.88 | −130.10 | −124.5 | −124.8 | 0.998 |
| 0.90 | −107.66 | −103.8 | −104.0 | 0.998 |
| 0.92 | −85.53 | −83.1 | −83.2 | 0.999 |
| 0.94 | −63.70 | −62.3 | −62.4 | 0.999 |
| 0.96 | −42.17 | −41.6 | −41.6 | 1.000 |
| 0.98 | −20.94 | −20.8 | −20.8 | 1.000 |
| 1.00 | 0.00 | 0.0 | 0.0 | — |
| 1.00 | 0.00 | 0.0 | 0.0 | — |
| 1.02 | 20.65 | 20.8 | 20.8 | 1.000 |
| 1.04 | 41.02 | 41.6 | 41.6 | 1.000 |
| 1.06 | 61.10 | 62.3 | 62.4 | 0.999 |
| 1.08 | 80.91 | 83.1 | 83.2 | 0.999 |
| 1.10 | 100.45 | 103.8 | 104.0 | 0.998 |
| 1.12 | 119.72 | 124.5 | 124.8 | 0.998 |
| 1.14 | 138.72 | 145.1 | 145.6 | 0.997 |
| 1.16 | 157.46 | 165.7 | 166.4 | 0.996 |
| 1.18 | 175.94 | 186.3 | 187.1 | 0.995 |
| 1.20 | 194.17 | 206.7 | 207.9 | 0.994 |
| 1.22 | 212.15 | 227.2 | 228.7 | 0.993 |
| 1.24 | 229.88 | 247.5 | 249.5 | 0.992 |
| 1.26 | 247.37 | 267.8 | 270.3 | 0.991 |
| 1.28 | 264.61 | 288.0 | 291.1 | 0.989 |
| 1.30 | 281.62 | 308.1 | 311.9 | 0.988 |
| 1.32 | 298.40 | 328.1 | 332.7 | 0.986 |
| 1.34 | 314.94 | 348.0 | 353.5 | 0.984 |
| 1.36 | 331.25 | 367.8 | 374.3 | 0.983 |
| 1.38 | 347.34 | 387.6 | 395.1 | 0.981 |
| 1.40 | 363.21 | 407.2 | 415.9 | 0.979 |
| 1.42 | 378.86 | 426.7 | 436.7 | 0.977 |
| 1.44 | 394.30 | 446.1 | 457.5 | 0.975 |
| 1.46 | 409.52 | 465.4 | 478.3 | 0.973 |
| 1.48 | 424.53 | 484.6 | 499.1 | 0.971 |
| 1.50 | 439.34 | 503.7 | 519.9 | 0.969 |

FIG. 4 shows the outputs p, P and Q in relation to the variable z as shown in Table 1 (1) and 1 (2).

From this Figure, it will be seen that the ionization current I of the ionization chamber 13 for the density measurement is conveted into an approximately linear output signal P. The approximation error $|1-(P/Q)| \cdot 100\%$ in the region of density fluctuation of ±20% from $z=1$, which is often observed in cigarettes, is not greater than 0.7%. This approximation error is extremely small considering that the error $|1-(p/Q)| \times 100\%$ is 7.2% when the system according to the invention is not used.

When the constant to be multiplied by the circuit 40 is zero the approximation is as large as that obtained when this system is not used. It is found that the approximation error decreases as the value of the constant increases from zero, and becomes minimum when it is equal to $\frac{1}{2}I_T$. The error increases again as the value of the constant increases further and, when it is equal to $1/I_T$, the error becomes the same level as that obtained when this system is not used.

The signal P derived from the output terminal 61 is delivered to the integral holding circuit 70 and is integrated by the latter for each cigarette. The integrated signal which represents the weight of each cigarette is then delivered to the comparator 91 and compared with the reference weight signal. When the voltage of the weight signal is lower than that of the reference weight signal, i.e. when the cigarette is unsatisfactory, the comparator 91 delivers its digital output signal to the shift register 94 which in turn activates the rejection valve 96 after a predetermined time interval to reject the unsatisfactory cigarette.

The fluctuation in the cigarette weight signal is obtained in the integral holding circuit 70 is simulated using a computer by dividing the length corresponding to the length of a cigarette into 100 sections, generating normal random numbers corresponding to respective sections and applying noise signals obtained from the radiation source to the random numbers. Then, the standard deviation δ is calculated for the case in which the density signal is integrated after it is converted into a linear signal and the conventional case in which the density signal is integrated without the conversion. The result of the simulation shows as follows.

| True standard deviation: | δ = 2.3% |
|---|---|
| Standard deviation without this system: | δ = 2.56% |
| Standard deviation with this system: | δ = 2.4% |

If the threshold for rejecting unsatisfactory cigarettes is set at the point 2δ, it is possible to achieve a savings in tobacco of 2×(2.56−2.4)=0.32%. Thus, the system according to this invention advantageously saves tobacco which constitutes the largest factor of the cost of cigarettes.

What is claimed is:

1. A material density radiological measurement system comprising a material density radiological detector having a radiation souce for density measurement, an ionization chamber for density measurement, and a means for generating a reference density signal, said detector producing an output signal from a difference of an output signal of said ionization chamber for density measurement and said reference density signal;
    a squaring circuit connected to the output terminal of said detector;
    a constant multiplying circuit connected to the output terminal of said squaring circuit, said constant being predetermined to have a value which is smaller than the reciprocal of an ionization current obtained when the density of a material to be measured is equal to the reference density; and
    a subtracting circuit, which input terminals being connected to the output terminals of said detector and said constant multiplying circuit, respectively.

2. A material density radiological measurement system according to claim 1, wherein said means for generating a reference density signal comprises a reference radiation source, a reference density material, and an ionization chamber for generating a reference density signal.

3. A material density radiological measurement system according to claim 1, wherein said means for generating a reference density signal comprises a means for setting a constant voltage.

* * * * *